United States Patent
Ralls et al.

[11] Patent Number: 5,885,076
[45] Date of Patent: Mar. 23, 1999

[54] METHOD AND SYSTEM FOR REMOVING MERCURY FROM DENTAL WASTE WATER

[75] Inventors: Stephen Alden Ralls, Great Lakes; William Corry Roddy, Grayslake; Ernest David Pederson, Lake Villa, all of Ill.

[73] Assignee: The United States of America as represented by the Secretary of the Navy, Washington, D.C.

[21] Appl. No.: 566,391

[22] Filed: Dec. 1, 1995

[51] Int. Cl.$^6$ ................................................ A61C 17/04
[52] U.S. Cl. .......................................... 433/92; 210/532.1
[58] Field of Search ................................. 433/91, 92, 95; 210/294, 295, 299, 532.1; 604/319–321

[56] References Cited

U.S. PATENT DOCUMENTS

| | | |
|---|---|---|
| 3,138,873 | 6/1964 | Bishop . |
| 3,482,313 | 12/1969 | Stram ......................................... 433/92 |
| 3,665,682 | 5/1972 | Ciavattoni et al. ......................... 55/337 |
| 3,777,403 | 12/1973 | Ritchie . |
| 3,847,573 | 11/1974 | Gandrud .................................. 433/92 |
| 3,870,483 | 3/1975 | Ritzler ...................................... 433/92 |
| 4,097,381 | 6/1978 | Ritzler ...................................... 210/259 |
| 4,385,891 | 5/1983 | Ligotti . |
| 4,580,978 | 4/1986 | Motola et al. ............................. 433/92 |
| 4,919,826 | 4/1990 | Alzner ...................................... 433/92 |
| 5,017,135 | 5/1991 | Meyer . |
| 5,114,578 | 5/1992 | Sundstrom . |
| 5,205,743 | 4/1993 | Ludvigsson . |
| 5,330,641 | 7/1994 | Cattani ...................................... 433/92 |
| 5,484,282 | 1/1996 | Trawoger et al. ......................... 433/92 |

FOREIGN PATENT DOCUMENTS

| | | | |
|---|---|---|---|
| 333672 | 9/1989 | European Pat. Off. ................. | 433/92 |
| 333673 | 9/1989 | European Pat. Off. ................. | 433/92 |
| 480881 | 4/1992 | European Pat. Off. ................. | 433/92 |
| 3813264 | 11/1988 | Germany ................................ | 433/92 |
| 4205936 | 9/1993 | Germany ................................ | 433/92 |

*Primary Examiner*—Ralph A. Lewis
*Attorney, Agent, or Firm*—A. D. Spevack

[57] ABSTRACT

A dental waste collection method and system in which a slurry of water and solid waste particles, including amalgam containing mercury and soluble and suspended mercury and other heavy metals is fed into a settling tank in which particles of insoluble solid waste material settle by gravity for later extraction, disposal, or reclamation. The liquid wastes and suspended metal particulates also can be co-precipitated to remove small size insoluble particles entrained in the slurry and soluble mercury and other metals. The supernatant remaining in the tank is removed and passed through a treatment stage including at least one filter and, if needed ion exchange media, and is in a form clarified of the mercury such as to be able to be conveyed into a public sewer system.

15 Claims, 1 Drawing Sheet

METHOD AND SYSTEM FOR REMOVING MERCURY FROM DENTAL WASTE WATER

BACKGROUND OF THE INVENTION

1. Field of the Invention

The invention relates to a method and system or apparatus for removing insoluble particles of mercury containing amalgam and other metals and soluble and suspended mercury from a dental waste slurry.

2. Description of the Prior Art

Dental amalgam is a common dental restorative material which contains silver, zinc, copper, tin and mercury, and occasionally other metals. During the most commonly performed dental procedures, dental amalgam containing mercury is removed as waste material from the patient's mouth. Removal of the amalgam typically takes place by vacuum extraction as part of a rinsing liquid, such as water. The mercury removed is in the form of mercury-containing particulate matter and the soluble and suspended mercury-containing fraction. Other material such as saliva, blood, pieces of dental appliances, etc. are also removed to form a liquid waste water slurry.

Mercury is generally classified as a toxic material which requires special handling and disposal procedures. Since the removed dental amalgam contains mercury, a need exists to separate the mercury-containing particulate matter and the soluble and suspended mercury-containing fraction from the waste water slurry extracted from the patient's mouth prior to eventual discharge of the waste water into the public sewer system. After removal from the waste water slurry, the mercury-containing waste can then be disposed of or reclaimed.

Apparatus previously has been disclosed, such as in U.S. Pat. Nos. 3,777,403 to Ritchie and 4,385,891 to Ligotti which use different containers through which the mixture of liquid and solids are passed and the solids settle out under the force of gravity. While such is apparatus may be satisfactory for the collection of large particles from a dental waste stream slurry mixture, they are not specifically designed to sediment, and later remove, all mercury-containing particulate matter and allow treatment of soluble and suspended mercury in the waste stream. In these patents, soluble material does not settle out by force of gravity. Instead, it is entrained in the liquid stream which is usually treated like waste water and disposed of in a commercial drain system. This is not satisfactory since the contaminated liquid waste may cause eventual contamination of the water supply and violate local sanitary district regulations, or those of other agencies, for mercury levels in waste water. Also, the systems of these patents do not provide for treatment or removal of the mercury remaining in the supernatant after the settling of particles by gravity is completed.

Ludviggson et al. U.S. Pat. No. 5,205,743 discloses a system in which the waste material is collected in a suction stream and passed through filters. This does not provide for collection of liquid waste mixture expelled by a patient into a collection sink or collection and disposal of any soluble mercury. Bishop U.S. Pat. No. 3,138,873 uses a suction system which passes a liquid slurry of the waste material through a porous bag which traps and collects the solid particles and passes the liquid. This apparatus must have a compromise as to the size of the particles collected and the liquid flow rate as determined by the porosity of the bag. Also, it makes no provision to collect soluble mercury.

In Meyer U.S. Pat. No. 5,017,135, particles are separated from the waste liquid as it is drawn under suction force in a sharply turning path past a series of traps into which particles settle out under force of gravity. Here also, no specific provision is made for collection of small particles or soluble mercury. Sundstrom U.S. Pat. No. 5,114,578 passes a slurry of water, saliva and particles through a pre-settling tank, into which the larger particles settle, and then in an upward inclined path through a special filter formed by a bundle of plastic tubes. In using this arrangement it is difficult to collect and dispose of the smaller metal particles collected on the walls of the filter and filter plastic tubes and there is no provision for the treatment of the soluble mercury.

SUMMARY OF THE INVENTION

The present invention is directed to a method and apparatus for the collection and treatment of the waste slurry removed from a patient's mouth during a dental procedure. According to the invention, the waste slurry is collected by a settling tank. Water is added to the waste slurry in the tank to bring it to a predetermined level in the tank to optimize sedimentation. At this time, chemicals such as co-polymers can be added to the waste slurry to co-precipitate the soluble and suspended mercury. The waste slurry is allowed to stand for a time in the tank to undergo a sedimentation/co-precipitation process and deposit a sediment to the bottom of the settling tank. During the sedimentation phase, the mercury-containing particles, other metal-containing particles, co-precipitated insoluble and soluble particles and other debris initially settle on a cone at the bottom of the settling tank.

The sediment formed from all of this insoluble particulate material is directed from the cone on the bottom of the tank into a detachable waste collection container where the sediment ultimately accumulates. When the container is appropriately full over time, it is removed from the system and the collected sediment is ready for disposal or reclamation of the metals.

After the sedimentation takes place in the tank, the supernatant, or top portion of the liquid after sedimentation, is decanted and can be filter treated to remove particles left in the supernatant. Further treatment with ion exchange media or other suitable processes can be performed if required before the supernatant is discharged to the public sewer system.

The invention accomplishes substantially complete removal of all forms of mercury from the dental waste stream.

OBJECTS OF THE INVENTION

An object of the invention is to provide a method and system for efficient separation and removal of mercury-containing particles/compounds from a slurry containing dental waste produced as a result of certain types of dental procedures.

A further object is to provide a method and system capable of removing soluble and suspended mercury from a dental waste slurry through gravity sedimentation, co-precipitation, filtering and treatment with ion exchange media or other suitable processes.

An additional object is to provide a method and system capable of efficiently collecting substantially all of the mercury removed during dental procedures for reclamation or proper disposal.

BRIEF DESCRIPTION OF THE DRAWING

A more complete appreciation of the invention will be readily obtained by reference to the following Description of the Preferred Embodiments and the accompanying drawing in which like numerals in different figures represent the same structures or elements. The representations in each of the figures is diagrammatic and no attempt is made to indicate actual scales or precise ratios. Proportional relationships are shown as approximations.

DESCRIPTION OF THE PREFERRED EMBODIMENTS

Figure 1:
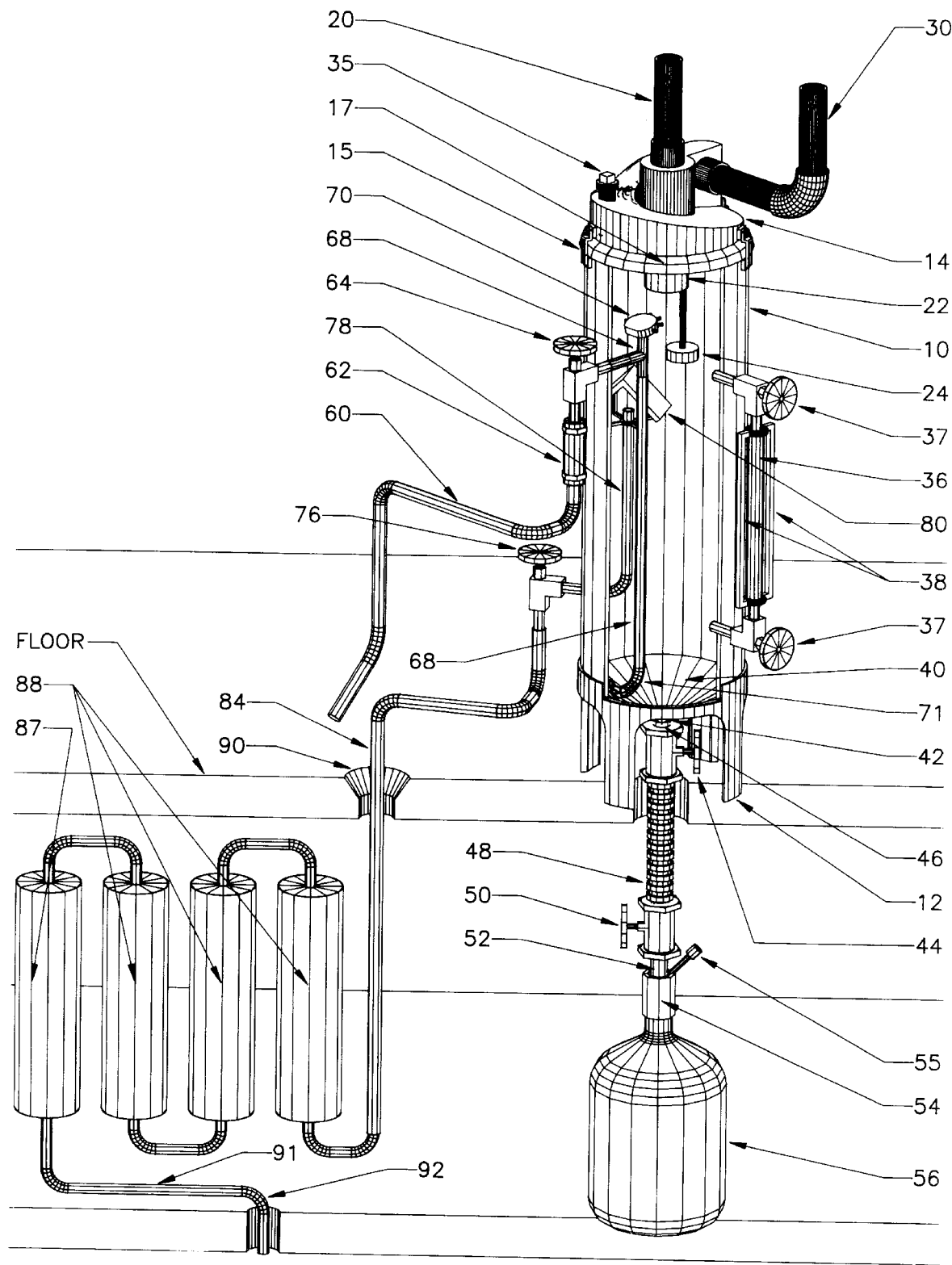
FIG. 1 is an overall diagrammatic view of the apparatus of the invention.

Referring to FIG. 1, a preferred embodiment of the system includes a settling tank 10 of a size necessary to handle the waste slurry of the number of dental operatories that are using the system. The tank 10 rests on and is removable from, or has an attached, base stand 12 whose legs are shown standing on a base surface such as a floor. As an alternative, the tank 10 can be mounted on a wall or other suitable support. The tank has a top cover 14 that is held to the tank by a plurality, for example three, of latches 15 spaced around the tank top and a gasket 17 is preferably provided between the cover and the tank.

Waste material produced during a dental procedure is normally removed from the patient's mouth through a vacuum line (not shown) under suction produced by vacuum turbines (also not shown). In addition, waste material can be placed by the patient into a sink (also not shown). As previously described, the waste material is in liquid slurry form and includes liquid components such as rinse water, saliva and blood and solid material such as pieces of teeth, particles of dental cement or bases, and pieces of restorative materials such as new and previously-placed mercury containing amalgam restorations. The mercury can be in the form of relatively large pieces, and smaller insoluble and soluble particles entrained in the waste slurry.

The waste slurry suction line serving the dental operatories attaches to a vacuum source connection 30 in the tank cover 14. An overflow shut-off valve 22 with a float 24 are attached internally of the tank to the end of the vacuum source connection 20 within the tank. Valve 22 doses the connection 20 to the vacuum turbines if the tank liquid level rises to where it could be aspirated into the suction turbines, thus causing damage to the turbines.

The cover 14 also has a capped opening/valve 35 through which materials, such as co-precipitates, can be added into the tank. Opening 30 is of a configuration so that the waste slurry enters the tank to minimize aspiration of the slurry through the open valve 22 connected to the vacuum turbines.

An external sight glass 36 is mounted on the exterior of the tank as a visual aid to determine the liquid level in the tank. The sight glass has a valve 37 at its upper and lower ends, normally left open, which can control liquid flow in the glass. The sight glass is protected laterally by metal rods 38 on each side of the glass.

There is an collection cone 40 at the bottom of the settling tank which has a drain opening 42 at its apex. Cone 40, which preferably has an angle of about 30 degrees, can be of metal or plastic or any other suitable material. The cone can be made as an integral part of the tank bottom. The tank bottom also could be made of conical shape. It is preferred that the tank and cone surfaces be made of a smooth material such as TEFLON, polypropylene, polyethylene or stainless steel or the interior of the tank and the cone be coated with a material, such as TEFLON, or another suitable smooth material. This facilitates the movement of solid material from tank cone 40 through a tube 48 connected to a detachable waste collection container 56.

Solid waste on the inner surface of the cone 40 is directed by gravity from the tank through a manually operated valve 44, such as a ball type valve, attached to a bulkhead fitting 46 connected to the cone drain outlet 42. A flexible tube 48 connects the outlet of valve 44 to the inlet of another valve 50, which also can be of the manually operated ball type.

Valve 50 has an outlet tube 52 that extends through a screw type cover 54 fastened to the top of a detachable waste collection container 56. The container 56 can be of any suitable material, such as polyethylene or polypropylene plastic, to afford a view of its contents so as to permit knowledge of when the container has to be removed and replaced. A drain tube with a screw cap 55, whose function is described below, is attached to cover 54.

Water input to the interior of the settling tank 10 is provided from an external source through a water intake pipe or flexible hose 60 and an (optional) rigid pipe adapter 62. Control of the water is by an input valve 64 mounted external of the tank. The outlet of valve 64, which is inside of the tank, supplies water to a rigid vertically extending connecting pipe 68 which has a respective outlet head 70 and 71 at each end. Water exiting from the upper head 70 sprays the interior of the upper part of the settling tank 10 to rinse particles and debris from its inner wall. The lower head 71 simultaneously sprays a stream of water around the cone to help direct debris collected on the cone 40 to its drain hole 42.

The tank has an outlet valve 76 which is connected to the lower end of a slotted "L" shaped discharge pipe 78 within the tank. The discharge pipe 78 starts at the level of valve 76 and extends upwardly to terminate at the approximate level of the maximum liquid level in the tank, which is marked near the upper end of the sight glass 36. The vertical portion of the discharge pipe 78 is slotted throughout its length on the side closest to the settling tank wall to minimize debris from collecting in it. This primarily allows only liquid above the valve 76 to be drained when tapping off the supernatant from within the tank. To minimize debris entering through the tank waste input 30 from collecting in the discharge pipe 78, a shield 80 is affixed to the top of the pipe to deflect debris away from the slot of the discharge pipe.

In the operation of the system, the waste slurry from the one or more connected operatories is collected in tank 10 during the workday. Typically, at the end of the day's work and after the vacuum turbines have been turned off, water is added to the liquid slurry of collected waste material in the tank 10 by opening valve 62. By using the sight glass 36 the water is added to the collected slurry to the level of a mark near the top of the sight glass. The water optimizes the sedimentation process. The waste slurry, which includes mercury-containing particles and soluble mercury, is allowed to settle undisturbed for 8 to 12 hours, for example overnight, over an approximate column height of 8 to 15 feet. This effectively is a sedimentation process and the resulting sediment follows the inner face of the conical collector 40 to the drain 42 and by gravity ultimately collects in the waste collection container 56.

During the sedimentation phase, precipitation of small particles containing mercury and soluble mercury is enhanced by using chemical complexing and/or co-precipitating agents, e.g., copolymers or metal complexing agents such as NALCO products 8186 and 93NP058. Co-precipitation agent(s) can be added to the settling tank through the access valve/opening 35 on the tank cover. Such agents would normally be added at the end of the workday (beginning of the sedimentation phase) prior to or while the internal liquid level is being adjusted with water to its maximum level.

The supernatant formed after the sedimentation step is tapped off, typically the following morning, through the outflow valve 76 and a hose 84. A discharge mark at the bottom end of the external sight glass 36 is used as a visual aid to achieve proper liquid level in the tank as the supernatant is drawn off.

Valve 44 at the conical collector outlet 42 and the valve 50 at the inlet to waste container 56 normally remain opened. This permits the sludge sediment, which contains the settled and precipitated mercury material collected at the bottom of the conical collector 40 to empty into the waste container 56.

When the container 56 becomes full, the ball valve 50 closest to the container cover 54 is closed. The container 56, which can have an approximately 3 to 5 gallon capacity depending upon the size of the installation, can be detached and disposed of as hazardous waste or the metals in it can be reclaimed. Any waste material which is trapped between valve 50 and the waste container cover 54 is decanted for treatment or disposal through drain tube 55 which is connected to the waste container cover 54. After removal of this trapped waste material, the container can be removed and capped for disposal or reclamation. An empty waste collection container 56 is then connected to the cover 54 and the drain tube 55 is re-capped. Valve 50 is opened and collection of mercury-containing particles resumed. The valve 44 positioned immediately under the settling tank 10 affords additional cutoff capability from tank 10.

The supernatant removed from tank 10 is conveyed through a discharge hose 84 to one or more filters 88 which can be, for example, of glass wool, sintered glass, porous clay or other suitable filter media. The material of filters 88 removes the remaining insoluble particles in the supernatant, including those created by the co-precipitant(s) used in the settling tank 10 which did not settle out during the sedimentation step or were trapped in the slotted pipe 78. The material of the filters preferably has a pore size ranging up to 50 microns. The filters can be of the type which are easily replaceable. After removal, the filters are disposed of in an approved manner since they contain mercury particles. The filters 88 can, as illustratively shown, be located on a floor below the floor on which tank 10 is located. A hose 84 passes through an opening 90 in the floor to the filter bank 88.

The filter process can be followed by ion exchange media 87 or other suitable processes for final treatment, if needed. This treatment removes additional soluble mercury material.

After the treatment is completed in filter 88, and ion exchange media 87 if used, the clarified liquid effluent is now, in most cases where mercury content regulations are in effect, pure enough to be disposed of directly into the public sewer system. This is schematically indicated by the hose 91 connected to the filter or ion exchange media outlet and emptying into a sewer inlet 92. In some cases, it may be desirable to treat the filtrate to remove any excess co-precipitates or other impurities.

The components of the system are made of any suitable material. Various fixtures and fittings can be made of brass, stainless steel, copper, plastic, PVC, fiberglass, polypropylene or polyethylene. The tubing and piping between the components are also of plastic, PVC, copper, rubber or equivalent material and can be either flexible or rigid. The settling tank 10 can be constructed of a suitable material, such as stainless steel or fiberglass, capable of providing rigid support.

The system is sized as needed to accommodate one or a plurality of dental operatory stations. For example, the vacuum outlets of a plurality of dental stations can empty into a single settling tank 10 of appropriate size. Additionally, the manually controlled water inlet valve 64 and supernatant outlet valve 76 can be adapted to a timer system and electronic valves to automate internal liquid levels. The cover access valve/capped opening 35 for adding co-precipitates also can be of the type to automate the addition of co-polymers or other chemicals to accommodate co-precipitation methodologies on the basis of time. The detachable waste container 56 and other components as shown in FIG. 1 on a different floor level from the settling tank 10, can be placed on the same level as the settling tank with minor modifications to the settling tank, plumbing and container design.

The system of the present invention was tested in an environment at which untreated mercury levels in the collected slurry were tested over a period of several weeks and mean values taken of a series of tests. The mean values were found to range from about 13.2 ppm to about 2763.4 ppm, with the mean of means of 671.6 ppm. After treatment with the system and method according to the invention, levels of remaining mercury were sampled 11 times over three weeks. The results are shown in Table 1, with the numbers in parentheses being the range of values. The filter used in the tests was made by KASCO. Average monthly levels of remaining mercury less than 0.05 ppm (<10,000 gallons per day) is currently acceptable for direct disposal into the sewer system of the local sanitary district involved.

TABLE 1

| Settling Tank Supernatant (ppm) | Filter Output (50–0.5 microns) (ppm) | Ion Exchange Media (ppm) |
|---|---|---|
| 0.46 (0.03–2.00) | 0.12 (0.05–0.20) | 0.034 (0.007–0.08) |

The mercury content in the liquid to be discharged into the sewer system can be further reduced by treating it in the settling tank 10 with a co-precipitant or combination of co-precipitants.

The principles described above can be readily modified or adapted for various applications without departing from the generic concept, and therefore such adaptations and modifications are intended to be comprehended within the meaning and range of equivalents of the disclosed embodiments. It is to be understood that the terminology and phraseology herein is for the purpose of description and not of limitation.

We claim:

1. A system for separating a slurry of dental waste into insoluble solid particles containing mercury and other metals, and a liquid phase including soluble mercury, and for cleaning the mercury and other metals from the liquid phase of the slurry comprising:

a settling tank having an upper end and a lower end said upper end having an intake means connected to dental sinks and aspirators, said settling tank receiving the slurry from the intake and holding the slurry while separation of the insoluble particles from the supernatant occurs and said lower end including a collector into which the insoluble particles settle by gravity action to produce an insoluble particulate sediment and a supernatant liquid above the sediment;

a valve located at the lowest point of the collector for removing the collected insoluble particulate sediment from said settlement tank and conducting the sediment to a removable sediment collection vessel;

discharge pipe means for withdrawing the supernatant from the upper portion of said tank; said discharge pipe being connected to;

filter and processing means for removing suspended particles and dissolved material from said supernatant producing clean effluent which flows through a discharge means to a sewage system.

2. A system as in claim 1 wherein said collector comprises a conical collector at the lower end of said tank.

3. A system as in claim 2 further comprising means for supplying a controlled and measured amount of water to the slurry in the settlement tank to optimize sedimentation.

4. A system as in claim 3 wherein said means for supplying water contains at least one outlet, said outlet washes the inner surface of the tank and directs sediment to said collector.

5. A system as in claim 4 wherein said means for supplying water contains two outlets, a first outlet for directing water to the inner wall of the tank at its upper end and a second outlet that washes the inner surface of the tank and directs sediment to said collector and from the surface of the collector into said removable sediment collection vessel.

6. A system as in claim 1 wherein said filter and processing means for removing suspended particles from the supernatant comprises at least one filter containing filter media.

7. A system as in claim 4 wherein said filter includes filter media having a pore size in the range up to 50 microns.

8. A system as in claim 6 further comprising an ion exchange means located in the supernatant flow path after the filter means for treating the supernatant to remove dissolved particles.

9. A system as in claim 1 further comprising means for adding at least one co-precipitant to the slurry in the settlement tank.

10. A system as in claim 9 wherein the at least one co-precipitant added to the water diluted slurry is of a type and of an amount to cause the treated supernatant output of the filter to be less than 0.05 ppm mercury.

11. A process for separating mercury from a dental waste water slurry including insoluble solid particles containing mercury and other metals, and soluble mercury, comprising the steps of:

supplying the slurry to a settling tank;

adding a predetermined amount of water to the settlement tank by raising the water level to a predetermined level in said settling tank;

permitting sedimentation of the slurry to settle the insoluble metal particles in said tank in the form of a sediment and leave unsettled insoluble particles of mercury entrained in a liquid supernatant;

removing a predetermined amount of the supernatant from the tank by lowering the water level to a predetermined level; and filtering the removed supernatant to remove the entrained insoluble particles.

12. A method as in claim 11 further comprising the step of adding at least one co-precipitant to the slurry in the tank to precipitate out the soluble and suspended mercury into the sediment.

13. A method as in claim 12 wherein the said at least one co-precipitant is a co-polymer. is a co-polymer.

14. A method as in claim 13 wherein the said at least one co-precipitant added to the water slurry is of a type and of an amount to cause the liquid output of the filter to be less than 0.05 ppm mercury.

15. A method as in claim 11, the water is added to the slurry in the tank at the commencement of the sedimentation step.

* * * * *